(12) United States Patent
Pollak et al.

(10) Patent No.: US 7,320,784 B1
(45) Date of Patent: Jan. 22, 2008

(54) IMMOBILIZED LABELING COMPOUNDS AND METHODS

(75) Inventors: Alfred Pollak, Lujbjana (SI); David Roe, Ontario (CA); Linda Fung Lu, Scarborough (CA); John Thornback, London (GB); Catherine M. Pollock, Toronto (CA)

(73) Assignee: Bracco Imaging S.p.A., Milan (IT)

( * ) Notice: Subject to any disclaimer, the term of this patent is extended or adjusted under 35 U.S.C. 154(b) by 0 days.

(21) Appl. No.: 09/913,401

(22) PCT Filed: Aug. 3, 1999

(86) PCT No.: PCT/CA99/00700

§ 371 (c)(1),
(2), (4) Date: Jan. 16, 2002

(87) PCT Pub. No.: WO00/48639

PCT Pub. Date: Aug. 24, 2000

(51) Int. Cl.
*A61K 49/00* (2006.01)

(52) U.S. Cl. ............ 424/9.1; 424/1.11; 424/1.37; 424/1.65; 424/9.3; 424/9.4; 424/9.5; 534/14

(58) Field of Classification Search ........... 424/1.11, 424/137, 1.53, 1.65, 1.69, 9.1, 9.2; 534/10–16; 530/300
See application file for complete search history.

(56) References Cited

U.S. PATENT DOCUMENTS

| 5,659,041 | A | | 8/1997 | Dunn-Dufault et al. |
| 5,789,555 | A | | 8/1998 | Pollak |
| 6,027,711 | A | * | 2/2000 | Sharma ............... 424/1.69 |
| 6,406,297 | B1 | * | 6/2002 | Raymond et al. ........ 434/15 |
| 6,921,526 | B2 | * | 7/2005 | Hoffman et al. ......... 424/1.69 |

FOREIGN PATENT DOCUMENTS

| WO | WO 93 17719 A | 9/1993 |
| WO | WO 96 037427 A | 2/1996 |
| WO | WO 99 40947 A | 8/1999 |

OTHER PUBLICATIONS

Golub et al., Science, Oct. 15, 1999, pp. 531-537.*
Smith, C.J. et al. "Evaluation of a Novel N3S Chelation System for the Preparation of Tc-99m and Re-188 Labeled Biomolecules," *J. Nuclear Med.* (May 1998)) vol. 39, No. 5 Suppl.:215 : 45th Annual Meeting of the Society of Nuclear Medicine, Toronto, Ontario, Canada Jun. 7-11, 1998 Society of Nuclear Medicine.
Wong, Ernest et al. "Synthesis and Structural Characterization of Tc-99m and Re oxo Complexes with $N_1$-$N'_2S_1$ Peptidic Ligands." *J. Nuclear Med.*, (1997) vol. 38, No. 5 Supp.:148: 44th Annual Meeting of the Society of Nuclear Medicine, San Antonio, Texas, USA, Jun. 1-5, 1997.
Pollak, A., et al., "Inflammation with Novel Peptidic Technetium-99m Chelators Linked to a Chemotactic Peptide", J. Nuclear Med., vol. 35 (5) Suppl. Jun. 1994, 44P-45P, Proceedings of the 41st Annual Meeting, New York City, NY.
Knight, L.C., :Thrombus Imaging with Technetium-99m Synthetic Peptides Based upon the Binding of a Monoclonal Antibody to Activated Platelets, J. Nuclear Med. vol. 95 (2) Feb. 1994, 282-288.

* cited by examiner

*Primary Examiner*—Dameron L. Jones
(74) *Attorney, Agent, or Firm*—Kramer Levin Naftalis & Frankel LLP

(57) ABSTRACT

The invention includes methods and compounds for labelling conjugates with metals which comprise the steps of coupling the conjugate to a support surface; introducing a complex-forming metal to the support; and collecting the metal-conjugate complex released from the support. The metal catalyzes cleavage of the conjugate from the support upon complex formation resulting in a solutions substantially free of unlabeled conjugate.

39 Claims, 5 Drawing Sheets

SEQUENCE LISTING

<160> NUMBER OF SEQ ID NOS: 6

<210> SEQ ID NO 1
<211> LENGTH: 8
<212> TYPE: PRT
<213> ORGANISM: Artificial
<220> FEATURE:
<223> OTHER INFORMATION: Description of Artificial Sequence: Synthetic
      Peptide

<400> SEQUENCE: 1

Gln Trp Ala Val Gly His Leu Met
1               5

<210> SEQ ID NO 2
<211> LENGTH: 5
<212> TYPE: PRT
<213> ORGANISM: Artificial
<220> FEATURE:
<223> OTHER INFORMATION: Description of Artificial Sequence: Synthetic
      Peptide

<400> SEQUENCE: 2

Thr Lys Pro Pro Arg
1               5

<210> SEQ ID NO 3
<211> LENGTH: 4
<212> TYPE: PRT
<213> ORGANISM: Artificial
<220> FEATURE:
<223> OTHER INFORMATION: Description of Artificial Sequence: Synthetic
      Peptide

<400> SEQUENCE: 3

Arg Gly Asp Ser
1

<210> SEQ ID NO 4
<211> LENGTH: 4
<212> TYPE: PRT
<213> ORGANISM: Artificial
<220> FEATURE:
<223> OTHER INFORMATION: Description of Artificial Sequence: Synthetic
      Peptide
<220> FEATURE:
<221> NAME/KEY: MOD_RES
<222> LOCATION: (1)..(1)
<223> OTHER INFORMATION: dimethyglycine

<400> SEQUENCE: 4

Gly Ser Cys Gly
1

<210> SEQ ID NO 5
<211> LENGTH: 13
<212> TYPE: PRT
<213> ORGANISM: Artificial
<220> FEATURE:
<223> OTHER INFORMATION: Description of Artificial Sequence: Synthetic
      Peptide
<220> FEATURE:
<221> NAME/KEY: MOD_RES
<222> LOCATION: (1)..(1)
<223> OTHER INFORMATION: dimethyglycine

<400> SEQUENCE: 5

```
Gly Ser Cys Gly Ala Gln Trp Ala Val Gly His Leu Met
1               5                   10
```

<210> SEQ ID NO 6
<211> LENGTH: 9
<212> TYPE: PRT
<213> ORGANISM: Artificial
<220> FEATURE:
<223> OTHER INFORMATION: Description of Artificial Sequence:  Synthetic
      Peptide
<220> FEATURE:
<221> NAME/KEY: MOD_RES
<222> LOCATION: (1)..(1)
<223> OTHER INFORMATION: dimethyglycine

<400> SEQUENCE: 6

```
Gly Ser Cys Gly Thr Lys Pro Pro Arg
1               5
```

IMMOBILIZED LABELING COMPOUNDS AND METHODS

FIELD OF THE INVENTION

The invention relates to compounds and methods useful for generating metal-ligand complexes. The metal-labeled agents are useful in radiotherapy and as imaging agents in medical diagnostics.

BACKGROUND

The art of diagnostic imaging exploits compounds that in binding or localizing site selectively within the body, help to resolve the image of diagnostic interest. Diagnostic imaging agents are effective for targeting and imaging biological receptors. These diagnostic imaging agents incorporate radionuclide metals such as technetium and rhenium. The radionuclide metals are used to label targeting molecules, such as proteins, peptides and antibodies that localize at desired regions of the human body. Localization of these agents is detected by gamma camera analysis. As targeting agents, proteins and peptides can offer the tissue specificity required for diagnostic accuracy.

Labeling of these and other diagnostic agents with metal atoms is made difficult by their chemical structure. Conventional labeling techniques involve the formation of the metal complex in a solution of excess ligand which typically results in high levels of unlabelled ligand. For example, technetium labeling reactions yield approximately one labeled ligand for every thousand or more unlabeled ligand. For many radiodiagnostic agents there is a finite number of binding sites ie. receptors for which both the labeled and unlabeled diagnostic agent compete. This leads to poor imaging because the excess unlabeled ligands compete with the labeled ligands for the binding sites. As a result, the administration of larger doses of the agent is required to achieve an acceptable image. The administration of larger doses of the agent into a patient can lead to adverse effects. Targeting molecules often cause physiological changes when they bind or localize to specific sites. For example, the targeting molecule may be a peptide that binds to a receptor and agonizes or antagonizes receptor activity. Unlabeled peptide will still cause the physiological effect of agonizing or antagonizing receptor activity, however, the benefits of a metal labeled peptide will not be obtained.

Presently, high performance liquid chromatography (HPLC) is applied to enhance the concentration of labeled agent in the solution before it is administered. While enhancing concentration, this separation step requires additional time and expense. This makes the technique impractical for clinical use.

A method for labeling biological targeting molecules with radionuclide metals is described in U.S. Pat. No. 5,789,555. The method involves the steps of covalently linking a chelating portion of a biological targeting molecule to a solid support through a metal cleavable maleimide linker. When a radionuclide metal is introduced, it complexes with the chelating portion of the biological targeting molecule. This results in the release of the biological targeting molecule from the support yielding a labeled biological targeting molecule. This method provides a high ratio of labeled to unlabeled molecules (specific activity). However the use of the linker requires an extra step of coupling the linker to the support. The requirement of a linker is therefore a drawback of this method.

Many labeling methods require the formation of the free thiol. The thiols tend react with each other forming disulphides. Extra precautions need to be taken to avoid disulphide formation which results in the reduction of product attached to the surface and the need for extra purification before radiolabeling.

Many metal chelators contain a sulfur atom which participates in the chelating function. Sulfur atoms are commonly rendered unreactive by the use of protecting groups, one of which is acetamidomethyl. The sulfur is protected with an acetamidomethyl group. The sulfur protecting groups must be removed to provide a free thiol. The acetamidomethyl protecting group is removed from the sulfur through the use of mercuric acetate. Mercuric acetate coordinates to the sulfur which then possesses a slightly positive charge making the chelator a good leaving group. The excess mercuric acetate is removed by reaction with hydrogen sulphide. Mercuric acetate is quite toxic. Therefore the requirement to deprotect sulfur with mercuric acetate is a drawback.

The labeling method described in U.S. Pat. No. 5,789,555 makes use of organic solid supports that consist of a plurality of particles. The particles can be difficult to filter for the subsequent removal of the unbound and labeled biological targeting molecules. These supports are very susceptible to radiolytic degradation due the emission of Particles by certain radionuclide metals. These supports are also otherwise not chemically robust. This makes the solid support difficult to sterilize since sterilization is carried out at very high temperatures.

There is therefore a need for a solid support for labeling biological targeting molecules with a radionuclide metal that permits labeling be carried out in a single step without the need for linker group. There is a need for a solid support for labeling biological targeting molecules with a radionuclide metal that has increased chemical robustness, reduced radiolytic degradation, is easily sterilized, and labeled and has well defined loading characteristics. There is further need for such a solid support that can directly bind a protected thiol group to form a bound thiol thereby avoiding the formation of disulfides.

There is a further need for an improved system that employs a surface as a substitute for mercury so that no mercuric acetate needs to be used or subsequently removed in order to deprotect sulfur atoms. There is a need for such a system that eliminates a few synthetic steps as well as the presence of mercury in a reaction solution.

SUMMARY OF THE INVENTION

The invention includes a method of producing metal labeled imaging and radiopharmaceutical agent formulations having high specific activity. The invention includes labeling peptides (such as dimethylglycylserinylcysteinylglycine) or other organic molecules that are attached to a support surface, preferably gold, via a group of a molecule that binds the surface. The surface binding molecule is preferably the sulfur group of a cysteine (this cysteine will ultimately be a part of the metal chelate). During the labeling of the peptide with a metal, (which is preferably a radioisotope, such as $^{99m}$Tc), the complexation of the metal to the chelator, and hence to the sulfur of the cysteine, causes weakening of the gold-cysteine bond with the result that the metal complexed peptide leaves the surface and moves into solution. Uncomplexed peptides remain attached to the gold surface. The result of this selective cleavage from the surface is that the radiolabeled peptide is produced without added carrier giving a high specific activity formulation.

According to one aspect of the present invention, sulfur is initially de-protected to produce the free thiol using mercuric acetate. The de-protected peptide is then added to the gold. However, the gold surface also allows for the in situ formation of the bound thiol. Therefore, according to another aspect of the present invention, a novel method for in situ production of the bound thiol is employed. This method allows protected sulfur groups to be de-protected without having to use mercuric acetate.

This approach to the preparation of radiopharmaceuticals having high specific activity offers the following advantages over the use of polymer supported strategies:

Increased chemical robustness of the metal support surface

Elimination of the presence of mercuric acetate

Avoidance of unnecessary handling of the free thiol

Elimination of extra synthetic steps

Production of the bound thiol in situ

Reduced radiolytic degradation of the metal support surface

Ease of sterilisation

Ease of attachment of the HS-chelator-targeting molecule

Well defined loading characteristics (by virtue of the ability to vary the surface area)

The invention includes a compound useful for generating a complex-forming metal ion labeled agent, the compound including: a metal support surface, and a conjugate releasably bound to the support surface, wherein the conjugate is capable of coordinating with a complex-forming metal ion so that the conjugate is released from the support surface. In a preferred variant, the conjugate includes a ligand and a targeting molecule and the ligand incorporates:

(a) a surface binding group selected from the group consisting of a cysteine amino acid residue, a cysteine amino acid residue derivative, a thiol or thioether group attached to an organic molecule, an amino acid residue derivative including phosphorous and a phosphorous containing organic molecule, wherein the amino acid residue, amino acid residue derivative or organic molecule is capable of releasably binding to the support surface; and (b) at least one accessory group capable of coordinating with the complex-forming metal ion; wherein the conjugate is capable of coordinating with a complex-forming metal ion so that the conjugate is released from the support surface.

In another embodiment, the invention includes a method for generating a complex-forming metal ion labeled diagnostic agent or radiotherapeutic agent, including the steps of: (a) obtaining a compound according to any of claims 1 to 18; (b) contacting the compound with the complex-forming metal ion to form a coordinate bond between the complex-forming metal ion and the agent so that the complex-forming metal labeled agent is released from the support surface.

One variation of the invention includes a method for generating a complex-forming metal ion labeled diagnostic agent or radiotherapeutic agent, including transchelating a conjugate from a metal support surface to a complex-forming metal ion so that the conjugate is released from the metal support surface. The invention also includes a method for preparing a complex-forming metal ion labeled peptide including (a) bonding a peptide, polypeptide, peptide mimetic or polypeptide mimetic that includes (i) a cysteine amino acid residue, a cysteine amino acid residue derivative or a phosphorous amino acid residue derivative and (ii) at least one accessory group capable of coordinating with the complex-forming metal ion, to a metal support surface by the sulfur atom or phosphorous atom of the residue or derivative and (b) labeling the peptide, polypeptide or mimetic with a complex-forming metal so that the metal complexed peptide, polypeptide or mimetic is released from the support surface. Another aspect of the invention relates to a method for preparing a complex-forming metal ion labeled agent including (a) bonding an organic molecule that includes (i) a sulfur atom or a phosphorous atom and (ii) at least one accessory group capable of coordinating with the complex-forming metal ion, to a support surface by the sulfur atom or the phosphorous atom and (b) labeling the agent with a complex-forming metal so that the metal complex conjugate is released from the support surface.

The invention also includes a complex-forming metal ion labeled agent prepared according to the methods of the invention as well as compositions and pharmaceutical compositions including the agent. The invention also includes a composition including a technetium metal labeled agent, wherein the composition includes a specific activity greater than 10,000 Ci/mmol with 99m-technetium and greater than 3,000 Ci/mmol with 188-rhenium. A pharmaceutical composition for radiotherapy or imaging, including a carrier and a complex-forming metal ion labeled agent, wherein the agent is prepared without HPLC.

Another embodiment of the invention includes a kit for preparing a complex-forming metal ion labeled agent. The kit includes a metal support surface, a conjugate and a predetermined quantity of a complex-forming metal ion. The conjugate is capable of being releasably bound to the support surface and is capable of coordinating with the complex-forming metal ion so that the conjugate is released from the metal support surface.

The invention also includes a method of detecting the presence or assessing the severity of a disease, disorder or abnormal physical state in a mammal. The method includes the steps of: (a) administering an effective amount of a complex-forming metal ion labeled agent; and (b) detecting the presence or assessing the severity of the disease, disorder or abnormal physical state. Another embodiment includes a method of radiotherapy of a disease, disorder or abnormal physical state in a mammal including the steps of administering an effective amount of a compound useful for generating a complex-forming metal ion labeled agent.

The invention also includes a method for the preparation of a support surface for manufacturing a complex-forming metal labeled agent including electro or electroless metal plating or vapor deposition of a suitable thickness, of the metal onto an inorganic or polmeric substrate in the form of particles, sponges or sieves, fibers or surfaces with suitable surface area between about 1 and 10,000 cm$^2$.

BRIEF DESCRIPTION OF THE FIGURES

Preferred embodiments of the invention will be described in relation to the drawings in which:

FIG. 1 (*b*) a schematic figure showing transchelation of a conjugate from a gold surface to technetium.

DETAILED DESCRIPTION OF THE INVENTION

Figure 1A:
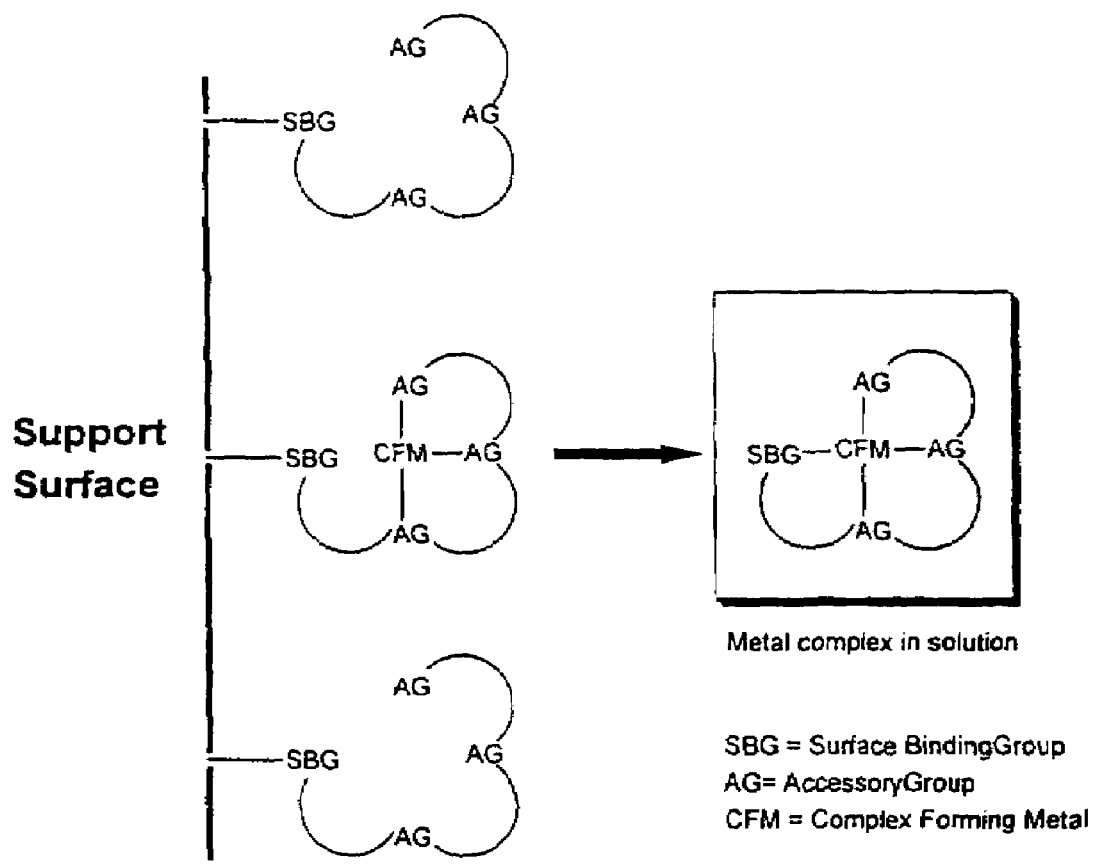
FIG. 1 (*a*) is a schematic figure showing transchelation of a conjugate (including surface binding group (SBG) and three accessory groups (AG)) from a metal support surface to a complex-forming metal (CFM)
Figure 1B:
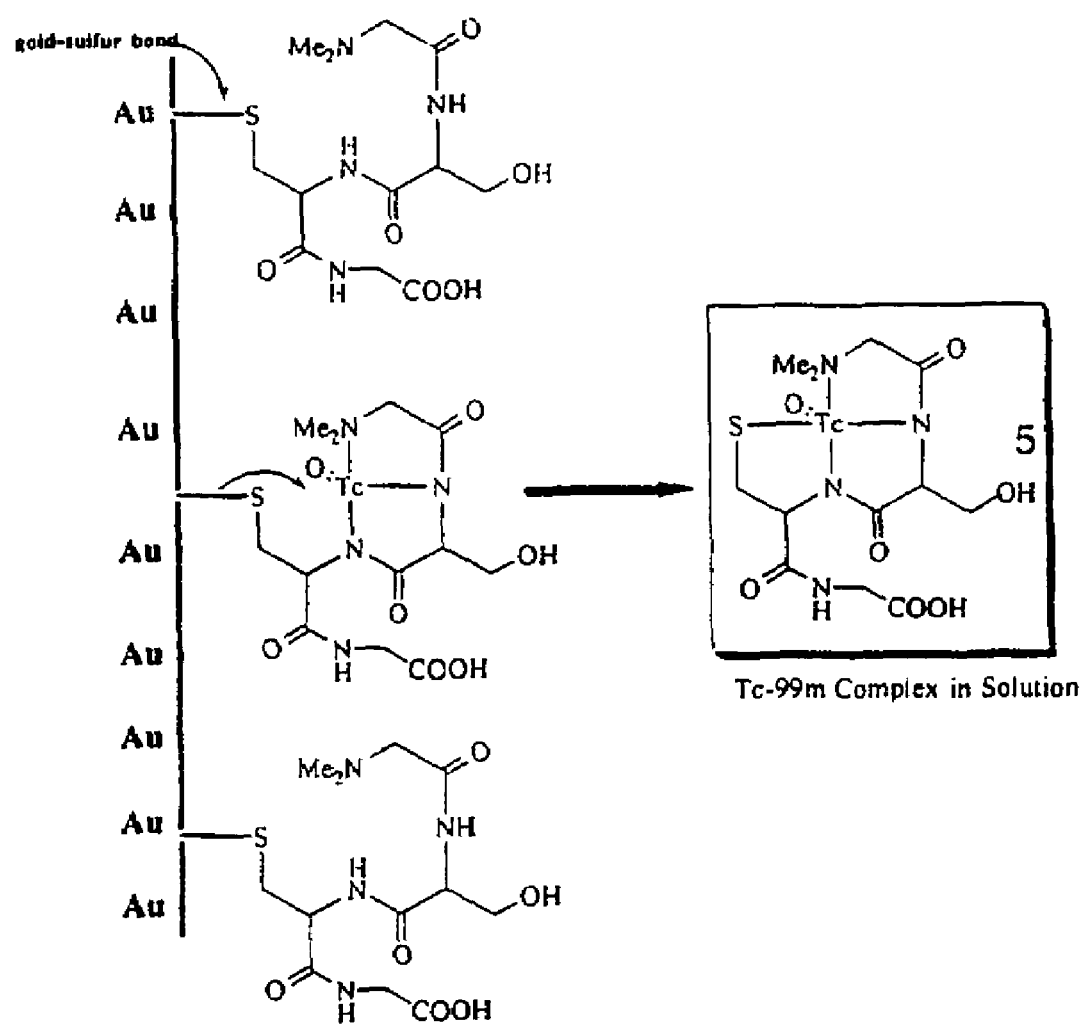

The present invention simplifies the process of generating a metal-ligand complex by coupling a conjugate to a support surface and transchelating the conjugate from the solid support to the metal. In a preferred embodiment, transchelation is from gold to technetium. The support surface preferably includes gold or an element having properties of binding to the metal cleavable conjugate that are similar to gold (gold is preferably Au(111)) so that a metal labeled radiotherapeutic agent or imaging agent can be formed. Metals with properties similar to gold include silver and copper. Preferably, the support surface is at least 50% metal, at least 90% metal and most preferably substantially pure metal (i.e. at least 99.9% metal). The support surface is preferably solid but may be semi-solid (for example, gold may be vapor deposited on a semi-solid compound, such as a soft plastic or resin). The step of introducing a metal to the support surface results not only in the formation of metal-support surface complexes, but also in the consequential release of those complexes from the support for collection in a form substantially free of uncomplexed conjugate. These processes are shown in FIGS. 1 (a) and 1 (b). Articles that describe materials and methods for binding molecules to gold include Bain et al., "Formation of Monolayer Films by the Spontaneous Assembly of Organic Thiols from Solution onto Gold[1]", American Chemical Society, 111, 321-335 (1989); Laibinis et al., "Comparison of the Structures and Wetting Properties of Self-Assembled Monolayers of n-Alkanethiols on the Coinage Metal Surfaces, Cu, Ag, Au[1]", American Chemical Society, 113, 7152-7167 (1991); Sasaki et al., "Two-Dimensional Arrangement of a Functional Protein by Cysteine-Gold Interaction: Enzyme Activity and Characterization of a Protein Monolayer on a Gold Substrate", Biophysical Journal, Volume 72, 1842-1848 (1997); Bain et al., "Correlations between Wettability and Structure in Monolayers of Alkanethiols Adsorbed on Gold[1]", American Chemical Society, 110, 3665-3666 (1988) which are incorporated by reference in their entirety.

Figure 2:
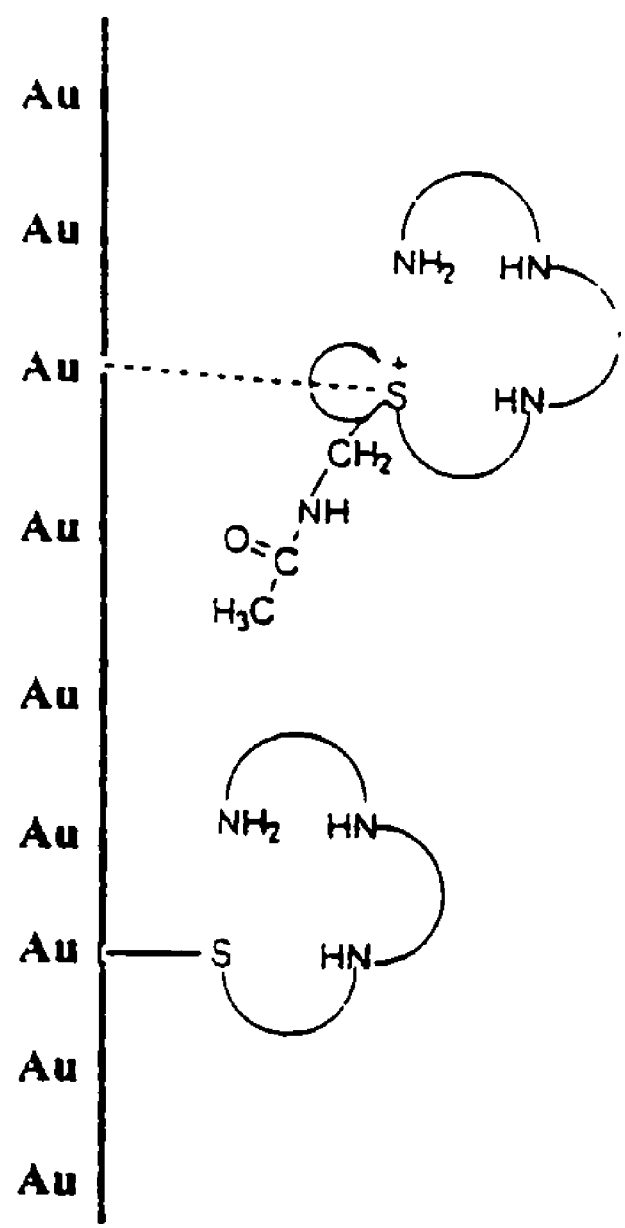
FIG. 2 is a schematic figure showing in situ production of a thiol bound to a gold surface

The present invention also permits the in situ formation of the bound thiol through binding to a gold surface. The protected sulfur atom binds to the gold surface resulting in the release of the protecting group as shown in FIG. 2.

Compound Aspects

According to an aspect of the present invention, compounds are provided that are useful for generating metal labeled imaging agents that are substantially free of the unlabeled imaging agent. The compounds include a metal support surface, and a conjugate releasably bound to the support surface. The conjugate is capable of coordinating with a complex-forming metal ion so that the conjugate is released (transchelated) from the support surface. The conjugate preferably includes a ligand and a targeting molecule. The conjugate is preferably a peptide, a polypeptide, a peptide for polypeptide mimetic (preferably a derivative) or an organic molecule. Those skilled in the art recognize that a variety of techniques are available for constructing peptide mimetics with the same or similar desired biological activity as a corresponding peptide or polypeptide compound of the invention but with more favorable activity with respect to solubility, stability, and/or susceptibility to hydrolysis and proteolysis. See for example, Morgan and Gainor, *Ann. Rep. Med. Chem.*, 24:243-252 (1989). The organic molecule is preferably a small organic molecule, having molecular weight less than about 600 Daltons and more preferably less than about 500 Daltons. The ligand may be a peptide, a peptide mimetic or a small organic molecule. The ligand preferably incorporates (a) a surface binding group selected from the group consisting of a cysteine amino acid residue, a cysteine amino acid residue derivative, a thiol or thioether group attached to an organic molecule, an amino acid residue derivative including phosphorus and a phosphorus containing organic molecule, wherein the amino acid residue, amino acid residue derivative or organic molecule is capable of releasably binding to the support surface; and (b) at least one accessory group capable of coordinating with the complex-forming metal ion. In a variation of the invention it is possible that one or more accessory groups is in the targeting molecule. The conjugate is capable of coordinating with a complex-forming metal ion so that the conjugate is released from the support surface. The conjugate preferably includes a peptide sequence such as a bombesin 7-14 fragment, QWAVGHLM (SEQ ID NO:1), TKPPR (SEQ ID NO:2), RGDS (SEQ ID NO:3), cyclopropylcarbonyl-nLe-L-F-W-E-K(GCSDMG)-G, an antibody (preferably monoclonal or polyclonal) antibody fragment and a small organic molecule that targets a receptor or a transporter.

The compound may optionally include a linker, which is, preferably, a biologically inert organic residue connecting the targeting molecule and the conjugate. Suitable linkers are allkyl, polyether, aromatic or polyaromatic compounds, with 3-100 atoms.

These compounds are useful for generating compositions (preferably imaging agent compositions or radiotherapeutic pharmaceutical compositions) with very high specific activity because they are substantially free of unlabeled agent.

Ligand Definition

The term "ligand" refers to compounds that incorporate at least one surface binding group. A surface binding group includes a sulfur or phosphorous atom (or atom with similar binding properties) which releasably binds to the support surface. In a preferred embodiment, the atom is sulfur which is capable of binding to gold to become a sulfide. The ligand also includes at least one accessory group, and preferably three of the accessory groups, capable of forming a coordinate bond with a given complex-forming metal, thereby forming a stable metal-ligand complex. The ligand preferably incorporates 3 accessory groups selected from the group consisting of (a) a nitrogen atom, an oxygen atom or a sulfur atom incorporated in an amino acid residue, (b) a nitrogen atom, an oxygen atom, a selenium atom, a phosphorous atom or a sulfur atom incorporated in an amino acid residue derivative, or (c) a nitrogen atom, an oxygen atom, a selenium atom, a phosphorous atom or a sulfur atom incorporated in an organic molecule or (d) a combination of one or more of (a) to (c), wherein the atoms have metal coordinating activity.

In the case where a ligand contains one accessory group and a surface binding group, the ligand may be referred to as a "chelator". Ligands that contain two or more accessory groups and a surface binding group, referred to as multidentate, typically form more stable metal-ligand complexes than do monodentate ligands and are preferred for this reason. Many ligands that bind to radionuclide metals are tetradentate containing a combination of four nitrogen and sulfur metal-coordinating atoms i.e. $N_3S$ and $N_2S_2$, however they may incorporate other metal-coordinating atoms such as oxygen, phosphorous and selenium (for example see FIG. 1 (a)). Preferred ligands of the invention include molecules incorporating a sulfur surface binding atom and at least 3 nitrogen atoms (for example see FIG. 1 (b)). The ligand preferably includes a peptide selected from the group consisting of a tetradentate $N_xS_{4-x}$ ligand, a tetradentate $N_xS_{4-x}$, ligand derivative, a polyamino polysulfide and a polyamino polysulfide derivative.

For radiotherapy and diagnostic imaging it is particularly desirable that the metal complex is highly stable in vivo so that the metal is not released from the ligand in substantial quantities to accumulate in tissues. The present invention can be applied to a wide variety of ligands, such as $N_3S$ chelators described in PCT application PCT/CA94/00395 and $N_2S_2$ chelators described in PCT application PCT/CA94/00479. Preferred ligands are peptides or derivatives thereof which incorporate a pendant sulfhydryl group for binding to a metal. Suitable peptidic chelators are those described in WO 9317719 which are amenable to coupling to targeting molecules, particularly targeting molecules that are also peptidic. In one embodiment, the invention is applied to label ligands that have intrinsic targeting properties. One such ligand available for radiodiagnostic imaging is mercapto-acetyl-glycyl-glycyl-glycine (MAG3) which localizes in renal tissue and may be labeled according to the method of the present invention to prepare renal imaging or radiotherapeutic agents. MAG3 is an $N_3S$ class of ligand having three nitrogen coordinating atoms and one sulfur coordinating atom.

Targeting Molecule

Targeting molecules suitable for use in compounds of the invention are compounds that are capable of localizing selectively in vivo at sites for imaging such as at a particular organ, tissue or cell type. Suitable targeting molecules include a polypeptide, a peptide, a nucleic acid molecule, an oligonucleotide, a saccharide, an oligosaccharide, a steroid, a cyclic peptide, a peptide or polypeptide mimetic, an enzyme substrate, an inhibitor and a small organic molecule. Preferred targeting molecules include polypeptides and peptides, particularly those capable of binding with specificity to cell surface receptors characteristic of a particular pathology. The targeting molecule is preferably a molecule having agonist or antagonist activity. The targeting molecule preferably includes a molecule selected from the group consisting of a bombesin 7-14 fragment, QWAVGHLM (SEQ ID NO:1), TKPPR (SEQ ID NO:2), RGDS (SEQ ID NO:3) and small organic molecule that targets a receptor or a transporter. The receptor or transporter is preferably a dopamine receptor or transporter, a serotonin receptor or transporter, a sigma receptor, a GABA receptor, a nicotinic receptor, a cholinergic receptor, a norepinephrine receptor or transporter, a glucose transporter and an opioid receptor. Other preferable targeting molecules are peptides, polypeptides or derivatives comprising 3 or more amino acid residues that bind to cell surface receptors such as those described PCT/CA94/00395. Preferably, targeting molecules are peptides comprising about: 3 to 1000, 3 to 500, 3 to 100, 3 to 50 amino acids and more preferable 3 to 10 or 3 to 6 amino acids. Small organic molecules of preferably about: 6 to 500, 6 to 250, 6 to 100 carbons and more preferably about 6 to 50 or 6 to 25 carbons are also useful targeting molecules. In an embodiment, targeting molecules are chemotactic peptides that bind to cell surface receptors and in particular are chemotactic peptides that incorporate the amino acid sequence cyclopropylcarbonyl-nLe-L-F-W-E-K(GCS-DMG)-G.

In the particular process aspect of the invention, it is desirable that the targeting molecule itself be free of metal binding sites such as pendant sulfhydryl groups. A ligand-targeting molecule conjugate labeled according to this particular process wherein the targeting molecule presents metal binding sites such as pendant sulfhydryl groups found in cysteine residues may 1) lose some or all of its localizing activity and 2) release metal in vivo thereby increasing background noise and obscuring the image.

Ligands and/or targeting molecules that are peptidic are commercially available or may be synthesized de novo by solid phase techniques or by recombinant DNA techniques. Solid-phase peptide synthesis generally involves the use of automated synthesizers and an appropriate support as the solid phase, to which is attached the C-terminal amino acid of the desired peptide. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of the peptide from the support, and the peptide is then isolated. Common purification techniques include reversed-phase HPLC using acetonitrile as solvent and trifluoroacetic acid as an ion-pairing agent. Procedures are described in numerous publications. Reference may be made to Stewart and Young, *Solid Phase Peptide Synthesis,* 2nd Edition (and subsequent editions), 1984, Pierce Chemical Company, Rockford, Ill. which is incorporated by reference in its entirety. Alternatively, peptides may be synthesized in solution or on a solid phase in small blocks and subsequently ligated to give the desired sequence. Peptides incorporating amino acids that are not genetically encoded require synthetic techniques for preparation.

Support

The term "support surface" refers to any substrate that is insoluble and inert in labeling solutions and is a metal support surface which is either made of, or is coated with, gold, silver or copper or a metal capable of releasably binding and coordinating sulfur or phosphorous for forming a metal complex in preparation of labeled agents. Suitable compounds that may be coated with a metal include inorganic silicate glass, alkylamino functionalized controlled-pore glass, silica or alumina beads and organic polystyrene, polyacrylamide or sugar polymers such as Sephadex and agarose. The support surface may be provided as a powder, a solid piece of metal, a ball contained in a tube or as a coating on the inside of a vessel. For the purposes of generating metal-ligand complexes the metal support may be in a column that allows for easy passage, collection and filtration of the complex solution.

The invention also includes a method for the preparation of a support surface for manufacturing a complex-forming metal labeled agent comprising electro or electroless metal plating or vapor deposition of a suitable thickness of the metal onto a preferably inorganic or polmeric substrate in the form of particles, sponges or sieves, fibers or surfaces with suitable surface area preferable between about 1 and 10,000 $cm^2$. The thickness of the metal on the metal support surface is preferably greater than about 10 nm.

Metal

The term "complex-forming metal" refers to any metal atom that is in a state capable of forming stable coordination bonds with metal coordinating atoms of a ligand. Complex-forming metals include the transition metals, lanthamide metals and actinide metals. Complex-forming metals useful in preparing agents for radiotherapy or imaging are preferably the metals (or radioisotopes of the metals) Tc, Re, Mn, Fe, Co, Ni, Zn, Cd, Mo, W, Cu, Ag, Au, Ti, Hg, Cr and Rh.

For MRI, the complex-forming metal can be a paramagnetic metal atom such as divalent and trivalent chromium, manganese, iron, cobalt, nickel, copper, samarium. The more preferred complex-forming metals for MRI are those exhibiting a strong magnetic moment, such as manganese.

The halide salt, in particular chloride salt, or oxide of these complex-forming metals are forms capable of complexing with a desired ligand and are suitable for the present invention. Radionuclide labeled imaging agents employ complex-forming metal isotopes that include emitters such as rhenium-186 and -188; and γ-emitters such as technetium-99m. The complex-forming metal most preferred for radiodiagnostic imaging is technetium-99m due to its advantageous half life of 6 hours and inexpensive preparation from a molybdenum-99 generator. Technetium and rhenium labeling is accomplished by procedures established in the art. Either complex-forming metal may be introduced to the ligand in aqueous solution in oxo, dioxo or nitrido form, for example pertechnetate ($^{99m}TcO_4$) or perrhenate, with a suitable reducing agent such as stannous chloride. Technetium may also be reduced by electrochemical reduction. Alternatively, radiodiagnostic agents may be formed by a transchelation reaction which entails use of the complex-forming metal in the form of a weak metal complex such as technetium-gluconate, heptagluconate, tartrate or citrate to give a desired labeled ligand. Transchelation reactions are typically heated to facilitate conversion of technetium from the weak complex to a complex with the ligand, for example in a boiling hot water bath.

Method Aspects

According to a method of the present invention, ligand-targeting molecule conjugates are labeled with complex-forming metals to provide a solution substantially free from unlabeled conjugate. The method for generating a complex-forming metal labeled conjugate diagnostic agent or radiotherapeutic agent includes transchelating a conjugate from a metal support surface to a complex-forming metal ion so that the conjugate is released from the support surface. In general, the process comprises the steps of obtaining a compound in which the conjugate is coupled to a support surface via a metal-cleavable surface binding group; introducing a complex-forming metal to the support; and collecting the labeled conjugate released from the support. In this process the complex-forming metal forms a coordination bond with the surface binding group and the accessory group(s) of the ligand thereby cleaving the bond between the ligand atom and the support. As a result, only labeled conjugate is released from the support. The complex-forming metal labeled agent has very high specific activity >about 10,000 Ci/mmol with 99m-technetium and >about 3,000 Ci/mmol with 188-rhenium.

In one preferred embodiment, the method for generating a complex-forming metal labeled conjugate diagnostic agent or radiotherapeutic agent, includes (a) obtaining a suitable compound prepared as described in this application and (b) contacting the compound with the complex-forming metal ion to form a coordinate bond between the complex-forming metal ion and the agent so that the complex-forming metal labeled agent is released from the support surface. Preferably, the method includes collecting the complex-forming metal labeled agent so released.

In another embodiment, the gold surface is employed for in situ formation of the bound thiol. This eliminates several steps which are detrimental to subsequent kit formulation. These steps cause difficulties in ensuring sterility.

A preferred method for preparing a complex-forming metal ion labeled agent (eg. peptide or polypeptide) includes (a) bonding a peptide, polypeptide, peptide mimetic or polypeptide mimetic that includes (i) a cysteine amino acid residue, a cysteine amino acid residue derivative or a phosphorous amino acid residue derivative and (ii) at least one accessory group capable of coordinating with the complex-forming metal ion, to a metal support surface by the sulfur atom or phosphorous atom of the residue or derivative and (b) labeling the peptide, polypeptide or mimetic with a complex-forming metal so that the metal complexed peptide, polypeptide or mimetic is released from the support surface. The peptide, polypeptide, peptide mimetic or polypeptide mimetic is preferably between about 3 and 50 amino acid residues or amino acid residue derivatives.

A preferred method for preparing a complex-forming metal ion labeled organic molecule includes (a) bonding an organic molecule that includes (i) a sulfur atom or a phosphorous atom and (ii) at least one accessory group capable of coordinating with the complex-forming metal ion, to a support surface by the sulfur group or the phosphorous atom and (b) labeling the agent with a complex-forming metal so that the metal complex conjugate is released from the support surface. The organic molecule preferably includes between about 6 and 100 carbons.

The preferred support surfaces are as described above and include metals such as gold, silver, copper and a metal capable of releasably binding sulfur or phosphorous for forming a metal ion labeled agent. The complex-forming metal is preferably a metal or radioisotopic form of metal from the group of Tc, Re, Mn, Fe, Co, Ni, Zn, Cd, Mo, W, Cu, Ag, Au, Ti, Hg, Cr and Rh.

The invention also includes the complex-forming metal ion labeled agent product prepared according to a method of the invention.

Pharmaceutical compositions

The invention also includes compositions, preferably pharmaceutical compositions for radiotherapy or imaging, including an agent prepared according to a method of the invention. The agents and compositions are preferably prepared without HPLC. The invention provides a composition including an agent (prepared according to a method of the invention, or any other method) which includes 99m-technetium metal labeled agent (preferably prepared on a gold support surface), and which has a specific activity greater than about 10,000 Ci/mmol with 99m-technetium or greater than about 3,000 Ci/mmol with 188-rhenium. The agent is preferably a peptide such as dimethylglycylserinylcysteinylglycine or polypeptide or a mimetic (preferably a derivative) thereof. Pharmaceutical compositions may be formulated according to known techniques.

The invention includes a method of detecting the presence or assessing of the severity of a disease, disorder or abnormal physical state in a mammal comprising: (a) administering an agent or composition of the invention and (b) detecting the presence or assessing the severity of the disease, disorder or abnormal physical state. The presence or severity of the disease, disorder or abnormal physical state is detected or assessed with a technique selected from the group consisting of positron emission tomography, nuclear magnetic resonance imaging, scintigraphy, single photon emission computed tomography, perfusion contrast echocardiography, ultrafast X-ray computed tomography, and digital subtraction angiography. Preferably, the agent includes a $^{99m}Tc$ metal and binds to a receptor and the technique is single photon emission computed tomography. Suitable methods and materials for imaging are described in: Handbook of Nuclear Medicine second ed., 1993, Mosby Press, Frederic I. Datz; Fundamentals of Nuclear Pharmacy third ed., 1992 Springer-Verlag, Gopal B. Saha; Principles and practice of Nuclear Medicine second ed., 1995, Mosby press, Paul J. Early and D. Bruce Sodee; which are incorporated by reference in their entirety.

The invention also includes a method of radiotherapy of a disease, disorder or abnormal physical state in a mammal including administering an agent or composition of the invention. Methods of performing radiotherapy are described in, for example, Principles and Practice of Nuclear Medicine, $2^{nd}$ Ed., P. J. Early and D. B. Sodee, Chapter 32, which is incorporated by reference in its entirety.

The pharmaceutical compositions are used to treat diseases and provide images in diseases, disorders or abnormal physical states including oncological, neurological, inflammatory, infection, and degenerative diseases. Other diseases, disorders and abnormal physical states will be apparent to those skilled in the art and/or on review of this application or references cited in this application.

Pharmaceutical compositions used for imaging or to treat patients having diseases, disorders or abnormal physical states preferably include an agent of the invention and an acceptable vehicle or excipient (Remington's Pharmaceutical Sciences $18^{th}$ ed, (1990, Mack Publishing Company) and subsequent editions). Vehicles include saline and D5W (5% dextrose and water). Excipients include additives such as a buffer, solubilizer, suspending agent, emulsifying agent, viscosity controlling agent, lactose filler, antioxidant, preservative. The compositions may further include a reducing agent, a bulking agent or a pH stabilising agent. There are preferred excipients for stabilizing peptides for parenteral and other administration. The complex-forming metal labeled agent is preferably administered by an intravenous parenteral route. The excipients preferably include serum albumin, glutamic or aspartic acid, phospholipids and fatty acids. Parenteral (injectable) administration is preferred. The methods for the preparation of pharmaceutically acceptable compositions which can be administered to patients are known in the art.

The pharmaceutical compositions can be administered to humans or animals (preferably mammals). Dosages to be administered depend on individual patient condition, indication of the drug, physical and chemical stability of the drug, toxicity, the desired effect and on the chosen route of administration (Robert Rakel, ed., Conn's Current Therapy (1995, W.B. Saunders Company, USA)). Preferably the amount of complex-forming metal labeled agent administered to the mammal is about 0.01 mcg/kg/minute to 1,000 mcg/kg/minute and more preferably about 0.01 to 50 mcg/kg/minutes.

Kits

The invention also includes kits for preparing a complex-forming metal ion labeled agent. The kit preferably includes a metal support surface, a conjugate and a predetermined quantity of a complex-forming metal ion, the conjugate being capable of being releasably bound to the support surface and capable of coordinating with the complex-forming metal ion so that the conjugate is released from the metal support surface. Suitable support surfaces, conjugates and complex-forming metal ions are described in this application or apparent to a person of skill in the art upon reviewing this application. The kit preferably includes a conjugate including a ligand and a targeting molecule. The ligand preferably incorporates (a) a surface binding group selected from the group consisting of a cysteine amino acid residue, a cysteine amino acid residue derivative, an organic thiol orthoether containing molecule, an amino acid residue derivative including phosphorous and a phosphorous containing aliphatic molecule, wherein the amino acid residue, amino acid residue derivative or aliphatic molecule is capable of releasably binding to the support surface; and (b) at least one accessory group. The conjugate is capable of coordinating with a complex-forming metal so that the conjugate is released from the support surface. Preferable targeting molecules are described in this application. The polypeptides, peptides or other reagents may be lyophilized. Since the radioisotopic metals often have a very short half life, it is advantageous to omit them from the kit.

The support surface preferably includes a metal selected from the group consisting of gold, silver, copper and a metal capable of releasably binding sulfur or phosphorous for forming a metal complex. The complex-forming metal is preferably one or more of the metals and radioisotopic metal forms of Tc, Re. Mn, Fe, Co, Ni, Zn, Cd, Mo, W, Cu, Ag, Au, Ti, Hg, Cr and Rh.

Preferred embodiments of the invention are described below in examples which are not intended to in any way limit the scope of the invention.

EXAMPLE 1

Preparation of Dimethylglycylserinylcysteinylglycine

A solution of dimethylglycylserinylcysteinyl(Acetomidomethyl)glycine (RP414) (50 mg) and mercuric acetate (75 mg) in 30% acetic acid (2 mL) was stirred at room temperature for 3 h. Distilled water (2 mL) was added and $H_2S$ gas was slowly bubbled through the solution for 3 min causing a black precipitate (mercury sulfide). The solution was filtered through a 0.2 micron filter diluted with a further 2 mL of distilled water and lyophilised.

EXAMPLE 2

Preparation of dimethylglycylserineylcysteinylglycine (RP414-SH) Attached to a Gold Surface A piece of gold foil (50 micron thickness) measuring 1×5 cm was coiled into a spiral and placed into a test tube. To this spiral was added a solution of 20% nitric acid and the whole gently agitated for 2 h. The nitric acid was removed and the foil washed with distilled water (5 times 4 mL for 30 min each). The final portion of water was removed and the foil soaked in phosphate buffered saline (0.01 M) for 1.5h at pH 7. The phosphate was then removed immediately prior to addition of the thiol.

A solution of dimethylglycylserinylcysteinylglycine (RP414-SH) prepared as in example 1 (−50 mg) in phosphate buffered saline (3 mL) was adjusted to pH 7 using $KHCO_3/K_2CO_3$ buffer. This solution was added to the foil prepared above and the reaction mixture gently agitated at room temperature for 20 h under an argon atmosphere. The solvent was decanted off and the foil washed with successive portions (2 mL) of phosphate buffered saline (five portions for 30 min each) with gentle agitation. The final aliquot was retained for analysis by HPLC to ensure that all non-adsorbed RP414-SH was removed. The final aliquot was decanted off and the apparatus purged with argon ready for labelling with 99m-Tc. The peptide RP414-SH adsorbed to the gold surface was designated RP895.

Radiolabelling Method of Gold Surface 1.0 mL of saline was added to the above prepared RP895

1 OOPL of stannous gluconate was added (stannous gluconate is prepared by the addition of 20 uL of 20 mg/mL stannous chloride to 1.0 mL of 13 mglmL sodium gluconate)

approximately 10mCi of Tc-99m pertechnetate in 200 μL of saline was added to the reaction The reaction vessel was then shaken vigorously Allow the reaction to take place for 1 hour at room temperature Then incubate reaction for 30 minutes at 60° C.

The total reaction volume was 1.3 mL, a clear and colourless solution with a pH of 5.0 was achieved.

Figure 3:
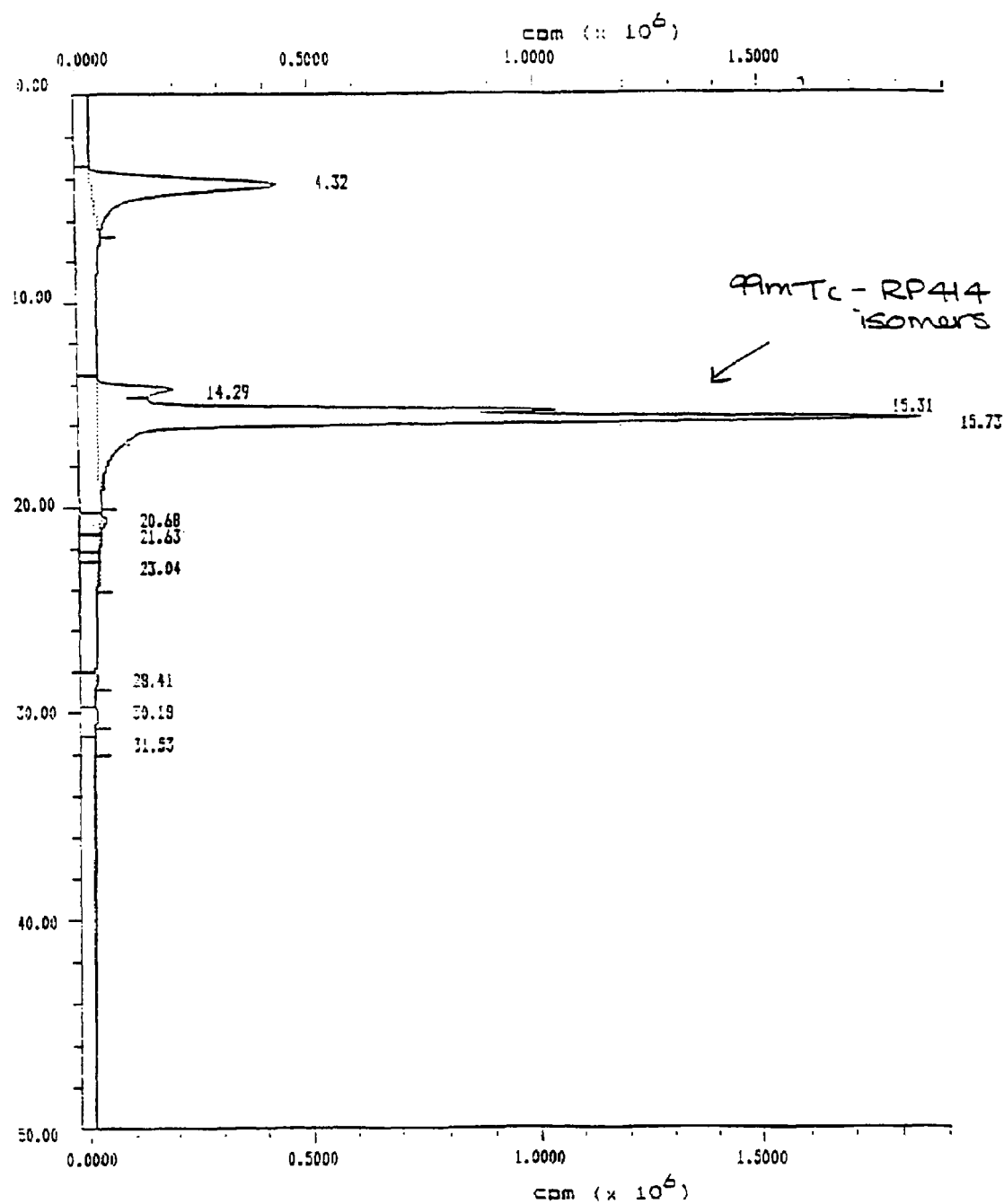
FIG. 3 is a radiometric trace of Tc-99m RP895(1) (Labeling of RP414)
Figure 4:
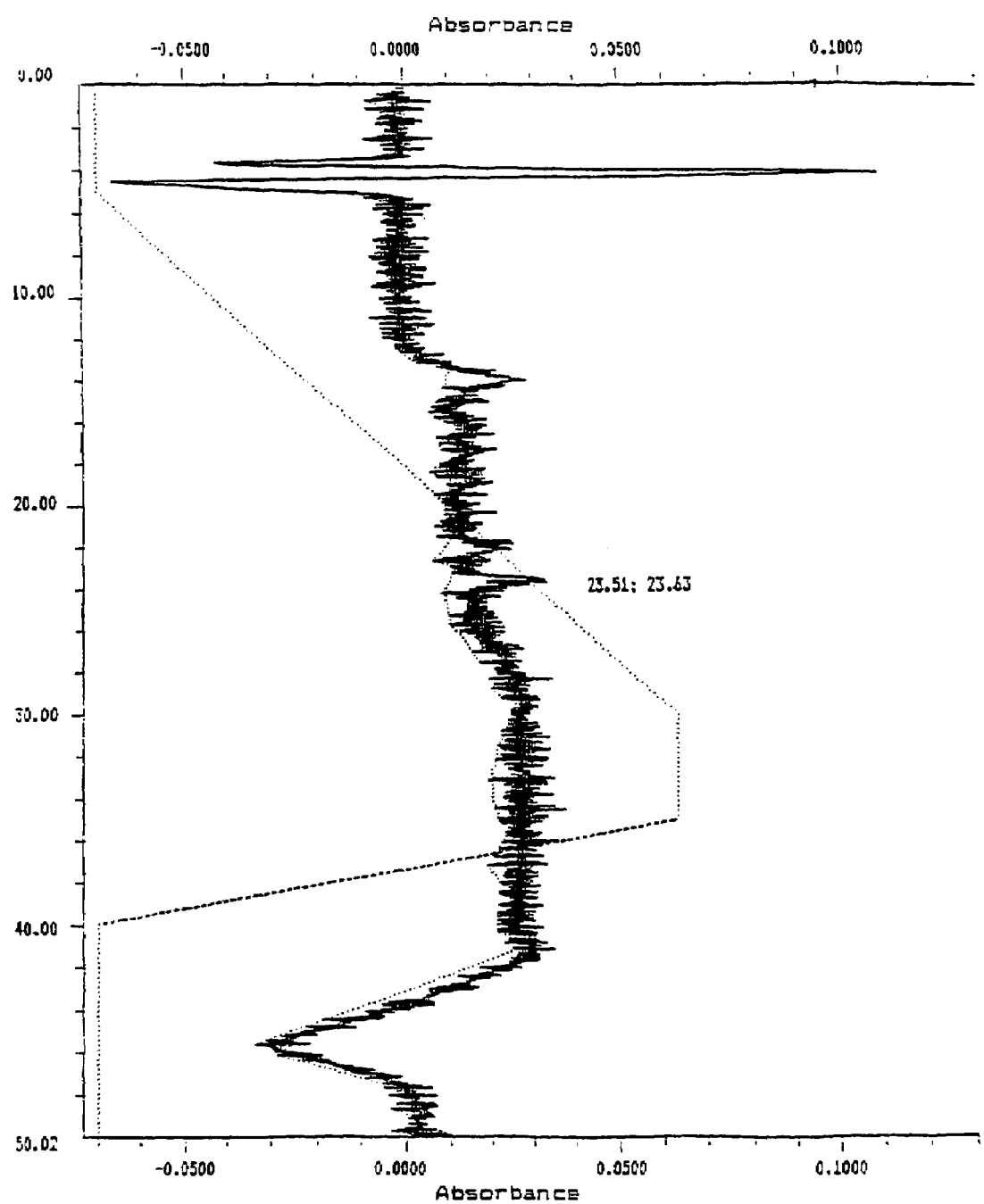
FIG. 4 is a ultraviolet light trace of Tc-99m RP895(1)

A 500 μL sample was analyzed using high performance liquid chromatography with a reverse phase C-18 column and a step gradient method of 0 to 70% acetonitrile w/0.1% TFA over 25 minutes. The sample was analyzed by both radiometric and UV detectors (see FIG. 3 for radiometric and FIG. 4 for UV of the final reaction.

EXAMPLE 3

Radiolabelling Method for RP414 on Gold Flakes (RP902)

15-830 mg of gold flakes loaded with RP414 was soaked in 1.0 ml of saline, followed by the addition of 0.1 ml of stannous gluconate and 0.1 ml of Tc-99m sodium pertechnetate (approximately 10 mCi). The reaction which contains a small stirrer was shaken vigorously and placed on a hot plate/stirrer to be incubated at 60-70° C. for 1 hour. An aliquot of the reaction mixture was removed and filtered through an acrodisc low protein binding 0.2 μm membrane filter. The filtered reaction was then analyzed using HPLC with a reverse phase C18 column and a step gradient of 0.1% TFA in both water and acetonitrile. The sample was analyzed by both radiometric and UV detectors.

EXAMPLE 4

Preparation of Dimethylglycine-Serine-Cysteine-Glycine on Solid Support

RP414 (dimethyglycine-serine-cysteine (Acm)-glycine) (SEQ ID NO:4) 50 mg was dissolved in 30% acetic acid and mercury acetate (75 mg) added. The mixture was stirred at room temperature for 3.5 hours. Hydrogen sulfide gas was bubbled through the solution with the formation of a black precipitate. This precipitate was removed by filtration and the solvents removed from the filtrate under reduced pressure.

Gold powder (2 micron average particle size) (75 mg) was wetted a drop of methanol in distilled water and the solution removed. The powder was then suspended in 20% nitric acid and shaken at 50C for 1.5h and after settling the supernatant removed. The powder was then washed with distilled water (4 times 5 mL for 30 min each) and then washed with phosphate buffered saline (2 mL). After removal of the saline a solution of de-protected RP414 in phosphate buffered saline (2 mL) was added and the mixture shaken at room temperature under argon for 20 h. The supernatant was removed and the gold powder washed with successive portions of phosphate buffered saline (5 times 4 mL).

EXAMPLE 5

Attachment of RP527-SH to Gold Flakes/Spheres (RP904)

Gold powder (1.5-3.0 micron particles, ~100 mg) was flamed using a bunsen burner. Methanol was added to the gold and stirred vigorously to break up the gold into fine powder. The suspension was centrifuged and the solution decanted.

RP527 (dimethylglycine-ser-cys(Acm)-gly-pala-gin-trp-ala-val-gly-his-leu-met-NH$_2$) (SEQ ID NO:5) (~10 mg, 1 eq) was dissolved in 30% acetic acid (4 mL) and then mercuric acetate (2.2 mg) was added. The reaction was left at room temperature for 3 hours and then bubbled through with hydrogen sulfide for 2 minutes. The resulting mixture was centrifuged and the solution decanted from the pellet of mercury sulfide. The solvent was removed in vacuo. RP527-SH(~10 mg) was then dissolved in a 1:1 solution of ethanol: 0.01 PBS and added to the gold powder in a vacutainer with vigorous stirring (magnetic stirbar was added). The solution was flushed with argon for 10 minutes and left under argon at room temperature for 24 hours. The reaction mixture was centrifuged and the supernatant removed. The powder washed with a 1:1 mixture of ethanol:aqueous 0.1% trifluoroacetic acid (5×4 mL), centrifuging between each addition of washing solution. The final aliquot was decanted off and the gold was dried in vacuo. It was purged with argon and stored at −20° C. in preparation for labeling with Tc-99m.

Radiolabelling Method for RP527(dimethyglycine-ser-cys(Acm)-gly-βala-gln-trp-ala-val-gly-his-leu-met-NH$_2$) on Gold Flakes (RP904)

100 mg of gold flakes loaded with RP527 was soaked in 1.0 ml of saline, followed by the addition of 0.1 ml of stannous gluconate and 0.1 ml of Tc-99m sodium pertechnetate (approximately 10 mCi). The reaction which contains a small stirrer was shaken vigorously and placed on a hot plate/stirrer to be incubated at 70-75° C. for 1 hour. An aliquot of the reaction mixture was removed and filtered through an acrodisc low protein binding 0.2 μm membrane filter. The filtered reaction was then analyzed using HPLC with a reverse phase C18 column and a step gradient of 0.1% TFA in both water and acetonitrile. The sample was analyzed by both radiometric and UV detectors.

EXAMPLE 6

Preparation of RP414 (dmG-S—C(Acm)-G) attached to gold foil (RP895)

A piece of gold foil (50 micron thickness, 1 cm×5 cm) was folded into an accordion shape and subsequently shaped into a cylinder. A solution of 20% nitric acid (4 mL) was added to the gold foil and heated at 40° C. for 2 h. The nitric acid was removed and the foil washed with distilled water (5×4 mL) for a few minutes. RP414 (~50 mg) was dissolved in 30% acetic acid (4 mL) and added to the gold in a vac tube. The solution was flushed with argon and left under argon at room temperature for 24 hours. The supernatant was removed and the foil washed with distilled water (5×4 mL). The final aliquot was decanted off and the vac tube was purged with argon in preparation for labeling with Tc-99m.

This experiment was repeated with RP128 (dmG-S-C(Acm)-G-T-K-P-P-R) (SEQ ID NO:6) attached to gold foil (RP905).

EXAMPLE 7

Preparation of Kit Formulation for RP895

A piece of gold foil (50 micron thickness, 1 cm×5 cm) was prepared and washed using the same procedure outlined in Example 1. RP414 (~50 mg) was loaded onto the gold using the same procedure outlined in Example 1. Once washed, labeling solution consisting of stannous gluconate (100 μL), stannous chloride (20 μL, 20 mg/mL) and sodium gluconate (1 mL, 13 mg/mL) was added, frozen and lyophilized.

EXAMPLE 8

Preparation of RP414 attached to gold powder (RP902)

Gold powder (1.5-3.0 micron particles, ~75 mg) was wetted with 5% methanol in water. The suspension was centrifuged and the solution decanted. The gold powder was washed with water (4 mL) and centrifuged. The water was decanted and 20% nitric acid was added to the gold. The suspension was heated at 40° C. for 2 h. The suspension was centrifuged and the nitric acid decanted. The powder washed with distilled water (5×4 mL), each time centrifuging between each addition of water. RP414 (~50 mg) was dissolved in 30% acetic acid (4 mL) and added to the gold powder in a vac tube with vigorous stirring (magnetic stirbar was added). The solution was flushed with argon and left under argon at room temperature for 24 hours. The supernatant was removed and the powder washed with distilled water (5×4 mL), centrifuging between each addition of water. The final aliquot was decanted off and the vac tube was purged with argon in preparation for labeling with Tc-99m.

EXAMPLE 8a

RP902 and RP904 were prepared as described in Example 8. However, the solution in which they were loaded onto the gold powder was changed to 1:1 ethanol:30% acetic acid. The final samples were lyophilized in preparation for labeling with Tc-99m.

EXAMPLE 8b

Gold powder (~75 mg) was loaded with de-protected RP414 in 1:1 ethanol: 0.01 M PBS. The rest of the reaction was carried out following the procedure in Example 8. This reaction was repeated for de-protected RP527.

EXAMPLE 9

Incremental Labeling of RP414 on Gold Powder (RP902)

A large batch of gold powder (1.5-3.0 micron particles, ~2g) washed and loaded with RP414 as described in Example 3. Ever increasing amounts were prepared for labeling with Tc-99m to investigate the efficiency of labeling as the amount of RP414 on gold powder was increased. Amino acid analysis was carried out on this batch of RP902.

Amounts of RP902 submitted for Tc-99m labeling:

7.85 mg, 17.9 mg. 34.4 mg, 78.8 mg, 151.3 mg and 308.6 mg

EXAMPLE 10

Methods of Radiolabelling Gold Compounds with Tc-99m Pertechnetate

Preparation of Stannous Gluconate:

0.02 mL of 20 mg/mL stannous chloride was added to 1.0 mL of 13 mg/mL sodium gluconate and shaken well 1. Radiolabelling Method for RP128 on Gold Foil (RP905)

A piece of RP905 was soaked with 1.5 mL of saline in a glass vacutainer. 0.1 mL of freshly prepared stannous gluconate was added as well as 0.1 mL of Tc-99m pertechnetate (approximately 10mCi). The reaction vessel was shaken vigorously and allowed to sit at room temperature for 1 hour. The final reaction volume was 1.7 mL and was clear and colourless with a pH of 4.5-5.5. An aliquot of the reaction was analyzed using HPLC with a reverse phase C-18 column and a step gradient method of 0 to 70% acetonitrile w/0.1% TFA over 25 minutes. The sample was analyzed by both radiometric and UV detectors.

The same method was repeated with RP414 on gold foil (RP895).

2. Radiolabelling Method for RP527 on Gold Foil (RP900)

A piece of RP900 was soaked with 1.0 mL saline in a glass vacutainer, followed by the addition of 0.1 mL of stannous gluconate and 1.0 mL of Tc-99m pertechnetate (approximately 10mCi). The reaction vessel was shaken vigorously and placed in a water bath for incubation at 55° C. for 1 hour. The final reaction solution was clear and colourless with a pH of 4.5-5.0. An aliquot of the reaction is analyzed using HPLC with a reverse phase C-18 column and a step gradient method of 0 to 70% acetonitrile w/0.1% TFA over 25 minutes. The sample was analyzed by both radiometric and UV detectors (wavelength=214 nm).

3. Radiolabelling Method for RP414 on Gold Powder (RP902)

75 mg of gold powder was loaded with RP414 was soaked in 0.5 mL of saline, followed by the addition of 0.1 mL of stannous gluconate and 0.1 mL of Tc-99m pertechnetate (approximately 10mCi). The reaction was then shaken vigorously and stirred in an oil bath at 55-60° C. for 1 hour. Care was taken when removing the reaction out of the water bath so as not to disturb the powder, which settled to the bottom of the container. This portion was then filtered through a 0.2% acrodisc filter to give a clear solution with a pH between 4.5-5.0. An aliquot of the reaction was analyzed using HPLC with a reverse phase C-18 column and a step gradient method of 0 to 70% acetonitrile w/0.1% TFA over 25 minutes. The sample was analyzed by both radiometric and UV detectors (wavelength=214 nm).

The same method was used for RP521 except the temperature and time of incubation was changed to 100° C. for 35 minutes.

The present invention has been described in detail and with particular reference to the preferred embodiments; however, it will be understood by one having ordinary skill in the art that changes can be made without departing from the spirit and scope thereof. For example, where the application refers to peptides, it is clear that polypeptides and proteins may often be used.

All publications, patents and patent applications are incorporated by reference in their entirety to the same extent as if each individual publication, patent or patent application was specifically and individually indicated to be incorporated by reference in its entirety.

We claim:

1. A composition for generating a complex-forming metal ion labeled conjugate, the composition comprising:
   (a) a metal support surface which is made of gold, silver or copper, or which is a substrate that is coated with gold, silver or copper, said substrate selected from the group consisting of inorganic silicate glass, alkylamino functionalized controlled-pore glass, silica, alumina beads, organic polystyrene, polyacrylamide, Sephadex, and agarose; and
   (b) a conjugate releasably bound to the support surface, the conjugate comprising a ligand and a targeting molecule;
wherein the conjugate coordinates with a complex-forming metal ion so that the labeled conjugate is released from the support surface.

2. The composition of claim 1, wherein the metal support surface releasably coordinates to sulfur or phosphorous and the ligand comprises a sulfur or phosphorous atom for binding to the metal support surface.

3. The composition of claim 2, wherein the ligand comprises a sulfur atom attached to a sulfur protecting group, wherein the metal support surface binds to the protected sulfur atom thereby releasing the sulfur protecting group from the sulfur atom and forming a thiol bond with the ligand.

4. The composition of claim 2, wherein the targeting molecule is selected from the group consisting of a peptide, a polypeptide, a peptide or polypeptide mimetic or an organic molecule having a molecular weight less than about 600 Daltons.

5. The composition of claim 4, wherein the targeting molecule is selected from the group consisting of a bombesin 7-14 fragment, QWAVGHLM (SEQ ID NO:1), TKPPR (SEQ ID NO:2) and RGDS (SEQ ID NO:3).

6. The composition of claim 4, wherein the targeting molecule comprises an organic molecule of 6 to 500 carbon atoms that targets a receptor or a transporter.

7. The composition of claim 2, wherein the ligand comprises:
   (a) a surface binding group selected from the group consisting of a cysteine amino acid residue, a thiol or thioester group attached to an organic molecule, an amino acid residue, and a phosphorous containing organic molecule, wherein the amino acid residue or organic molecule binds to the support surface; and
   (b) at least one accessory group that coordinates with the complex-forming metal ion, where the accessory group is selected from the group consisting of (a) a nitrogen, oxygen or sulfur atom incorporated in an amino acid residue; (b) a nitrogen, oxygen, selenium, phosphorous or sulfur atom incorporated in an amino acid residue; (c) a nitrogen, oxygen, selenium, phosphorous or sulfur atom incorporated in an organic molecule; and (d) a combination of one or more of (a) to (c), wherein the residues and/or molecules have metal coordinating activity.

8. The composition of claim 7, wherein the targeting molecule is selected from the group consisting of a peptide, a peptide mimetic, a polypeptide, a polypeptide mimetic and an organic molecule having a molecular weight less than about 600 Daltons.

9. The composition of claim 8, wherein the ligand is selected from the group consisting of a tetradentate $N_3S$ ligand, and a polyamino polysulfide.

10. The composition of claim 8, wherein the ligand comprises 3 accessory groups, each selected from the group consisting of (a) a nitrogen, oxygen or sulfur atom incorporated in an amino acid residue; (b) a nitrogen, oxygen, selenium, phosphorous or sulfur atom incorporated in an amino acid residue; (c) a nitrogen, oxygen, selenium, phosphorous or sulfur atom incorporated in an organic molecule; and (d) a combination of one or more of (a) to (c), wherein the residues and/or molecules have metal coordinating activity.

11. The composition of claim 1, wherein the targeting molecule has agonist or antagonist activity and is selected from the group consisting of a polypeptide, a peptide, a nucleic acid molecule, an oligonucleotide, a saccharide, an oligosaccharide, a steroid, a cyclic peptide, a peptide or polypeptide mimetic, an enzyme substrate, an inhibitor and an organic molecule having a molecular weight less than about 600 Daltons.

12. The composition of claim 1, wherein the targeting molecule is selected from the group consisting of a peptide, a polypeptide, a peptide or polypeptide mimetic or an organic molecule having a molecular weight less than about 600 Daltons.

13. The composition of claim 1, wherein the targeting molecule is selected from the group consisting of a bombesin 7-14 fragment, QWAVGHLM (SEQ ID NO:1), TKPPR (SEQ ID NO:2), RGDS (SEQ ID NO:3) and an organic molecule having a molecular weight less than about 600 Daltons that targets a receptor or a transporter.

14. The composition of claim 6 or claim 13, wherein the receptor or transporter is selected from the group consisting of a dopamine receptor or transporter, a serotonin receptor or transporter, a sigma receptor, GABA receptor, a nicotinic receptor, a cholinergic receptor, a norepinephrine receptor or transporter, a glucose transporter and an opioid receptor.

15. The composition of claim 3, wherein the metal support surface is gold.

16. The composition of claim 1, wherein the complex-forming metal is selected from the group of metals and radioisotopic metals consisting of Tc, Re, Mn, Fe, Co, Ni, Zn, Cd, Mo, W, Cu, Ag, Au, Ti, Hg, Cr and Rh.

17. The composition of claim 16, wherein the complex-forming metal is selected from the group of metals and radioisotopic metals consisting of Tc, Cu and Re.

18. A method of generating a complex-forming metal ion labeled conjugate for use as a diagnostic agent or radiotherapeutic agent, comprising: contacting the composition of claim 1 with a metal ion to form a coordinate bond between the metal ion and the conjugate so that the complex-forming metal labeled conjugate is released from the support surface.

19. The method of claim 18, further comprising collecting the labeled conjugate so released.

20. A technetium or rhenium labeled conjugate prepared using a composition of claim 1, wherein the conjugate is labeled with $^{99m}$Tc and has a specific activity of greater than 10,000 Ci/mmol or with $^{188}$Re and has a specific activity of greater than 3,000 Ci/mmol.

21. The composition of claim 20, wherein the conjugate comprises dimethylglycylserinylcysteinylglycine and a targeting molecule.

22. A pharmaceutical composition comprising a pharmaceutically acceptable carrier and the metal ion labeled conjugate of claim 20.

23. The pharmaceutical composition of claim 22 further comprising at least one agent selected from the group consisting of a reducing agent, a bulking agent and a pH stabilizing agent.

24. A method of imaging a mammal comprising:
  (a) administering an effective amount of the composition of claim 22; and
  (b) generating an image.

25. A method of radiotherapy in a mammal comprising administering an effective amount of the composition of claim 22.

26. The method of claim 24, wherein the composition is administered intravenously.

27. The method of claim 24, wherein the mammal is a human.

28. The method of claim 24, wherein the mammal is imaged by a technique selected from the group consisting of positron emission tomography, nuclear magnetic resonance imaging, scintigraphy, single photon emission computed tomography, perfusion contrast echocardiography, ultrafast X-ray computed tomography, and digital subtraction angiography.

29. The method of claim 28, wherein the technique is single photon emission computed tomography.

30. A kit comprising a metal support surface, conjugate and a predetermined quantity of complex-forming metal ion, the conjugate being releasably bound to the support surface and which coordinates with the complex-forming metal ion so that the conjugate is released from the metal support surface,
  wherein said metal support surface is made of gold, silver or copper, or is a substrate that is coated with gold, silver or copper, said substrate selected from the group consisting of inorganic silicate glass, alkylamino functionalized controlled-pore glass, silica, alumina beads, organic polystyrene, polyacrylamide, Sephadex, and agarose and the conjugate comprises a ligand and a targeting molecule.

31. The kit of claim 30, wherein the ligand comprises a sulfur atom attached to a sulfur protecting group.

32. The kit of claim 30, wherein the ligand comprises a sulfur or phosphorous atom for binding to the metal support surface.

33. The kit of claim 30, wherein the conjugate comprises a ligand and a targeting molecule, wherein the ligand comprises:
  (a) a surface binding group selected from the group consisting of a cysteine amino acid residue, a thiol or thioester group attached to an organic molecule having a molecular weight less than about 600 Daltons, and a phosphorous containing organic molecule, wherein the amino acid residue or organic molecule releasably binds to the support surface; and
  (b) at least one accessory group that coordinates with the complex-forming metal ion wherein the accessory group is selected from the group consisting of (a) a nitrogen, oxygen or sulfur atom incorporated in an amino acid residue; (b) a nitrogen, oxygen, selenium, phosphorous or sulfur atom incorporated in an amino acid residue; (c) a nitrogen, oxygen, selenium, phosphorous or sulfur atom incorporated in an organic molecule; and (d) a combination of one or more accessory groups.

34. The kit of claim 30, wherein the complex-forming metal is selected from the group of metals and radioisotopic metals consisting of Tc, Re, Mn, Fe, Co, Ni, Zn, Cd, Mo, W, Cu, Ag, Au, Ti, Hg, Cr and Rh.

35. The kit of claim 34, further comprising at least one agent selected from the group consisting of a reducing agent, a bulking agent and a pH stabilizing agent.

36. A method for generating a complex-forming metal ion labeled agent comprising:
  (a) providing a metal support surface which is made of gold, silver or copper, or which is a substrate that is coated with gold, silver or copper, said substrate selected from the group consisting of inorganic silicate glass, alkylamino functionalized controlled-pore glass, silica, alumina beads, organic polystyrene, polyacrylamide, Sephadex, and agarose;
  (b) providing a conjugate comprising a ligand and targeting molecule, wherein the ligand is selected from the group consisting of a peptide, a peptide mimetic, a polypeptide or a polypeptide mimetic of about 3 to 50 amino acid residues and includes a sulfur atom for binding to the metal support surface, the sulfur atom being protected by a sulfur protecting group;
  (c) contacting the protected sulfur atom with the metal support surface so that the sulfur atom forms a thiol bond with the metal surface thereby releasing the sulfur protecting group; and
  (d) contacting the ligand with the complex-forming metal ion to form a coordinate bond between the complex-forming metal ion and the ligand so that the complex-forming metal labeled agent is released from the support surface.

37. The method of claim 36, wherein the complex-forming metal is selected from the group of metals and radioisotopic metals consisting of Tc, Re, Mn, Fe, Co, Ni, Zn, Cd, Mo, W, Cu, Ag, Au, Ti, Hg, Cr and Rh.

38. The composition of claim 1, wherein the ligand comprises an organic molecule having a molecular weight of less than about 600 Daltons, when wherein said organic molecule comprises:
   (a) a sulfur atom in the form of a thiol or thioether group or a phosphorous atom where the sulfur or phosphorous atom binds to the support surface; and
   (b) at least one accessory group that coordinates with the complex-forming metal ion wherein the accessory group is selected from the group consisting of (a) a nitrogen, oxygen or sulfur atom incorporated in an amino acid residue; (b) a nitrogen, oxygen, selenium, phosphorous or sulfur atom incorporated in an amino acid residue; (c) a nitrogen, oxygen, selenium, phosphorous or sulfur atom incorporated in an organic molecule; and (d) a combination of one or more accessory groups.

39. The kit of claim 32, wherein the conjugate comprises a ligand and a targeting molecule, wherein the ligand comprises an organic molecule having a molecular weight of less than about 600 Daltons, wherein said organic molecule comprises:
   (a) a sulfur atom in the form of a thiol or thioether group or a phosphorous atom where the sulfur or phosphorous atom binds to the support surface; and
   (b) at least one accessory group that coordinates with the complex-forming metal ion wherein the accessory group is selected from the group consisting of (a) a nitrogen, oxygen or sulfur atom incorporated in an amino acid residue; (b) a nitrogen, oxygen, selenium, phosphorous or sulfur atom incorporated in an amino acid residue; (c) a nitrogen, oxygen, selenium, phosphorous or sulfur atom incorporated in an organic molecule; and (d) a combination of one or more accessory groups.

* * * * *